(12) United States Patent
Yamaoka

(10) Patent No.: US 7,374,908 B2
(45) Date of Patent: May 20, 2008

(54) MICROORGANISM AND PRODUCTION OF CAROTINOID COMPOUNDS THEREBY

(75) Inventor: Yukiho Yamaoka, Kure (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 541 days.

(21) Appl. No.: 10/492,475

(22) PCT Filed: Oct. 11, 2002

(86) PCT No.: PCT/JP02/10619

§ 371 (c)(1), (2), (4) Date: Apr. 12, 2004

(87) PCT Pub. No.: WO03/033683

PCT Pub. Date: Apr. 24, 2003

(65) Prior Publication Data

US 2004/0253724 A1    Dec. 16, 2004

(30) Foreign Application Priority Data

Oct. 16, 2001 (JP) .............................. 2001-318746
May 7, 2002 (JP) .............................. 2002-132190
Aug. 8, 2002 (JP) .............................. 2002-231126

(51) Int. Cl.
  *C12N 1/00* (2006.01)
  *C12N 1/12* (2006.01)

(52) U.S. Cl. .................. 435/67; 435/243; 435/946; 435/257.1

(58) Field of Classification Search .................. None
  See application file for complete search history.

(56) References Cited

U.S. PATENT DOCUMENTS

2001/0041358 A1    11/2001 Yokochi et al.

FOREIGN PATENT DOCUMENTS

| EP | 1138759 | * 10/2001 |
|---|---|---|
| JP | 2001-275656 | 10/2001 |
| JP | 2002-291464 | 10/2002 |
| WO | 01/62894 A2 | 8/2001 |

OTHER PUBLICATIONS

Rodriguez, et al., "Isolation of Astaxanthin From Marine Thraustochytrids (Zoosporic Marine Fungi)" Abstract of the General Meeting of the American Society for Microbiology, p. 1, May 1998.

Fontes, et al., "Growth Phase Dependence of the Activation of a Bacterial Gene for Carotenoid Synthesis by Blue Light" *The EMBO Journal*, vol. 12, No. 4, pp. 1265-1275, 1993.

Johnson et al., "Astaxanthin From Microbial Sources" *Critical Reviews in Biochemistry*, vol. 11, No. 4, pp. 297-326, 1991.

* cited by examiner

*Primary Examiner*—David M. Naff
*Assistant Examiner*—Deborah K. Ware
(74) *Attorney, Agent, or Firm*—Wenderoth, Lind & Ponack, L.L.P.

(57) ABSTRACT

It is intended to provide a process for conveniently and efficiently producing large amounts of astaxanthin and canthaxanthin from a material which can be easily obtained. A microorganism *Thraustochytrium* sp. CHN-3 (FERM P-18556) capable of producing astaxanthin and canthaxanthin, which belongs to the genus *Labyrinthula* and the *Thraustochytrium* species, is cultured and thus astaxanthin and canthaxanthin are accumulated in the microbial cells. Then the cells are separated from the medium and astaxanthin and canthaxanthin are collected from the separated cells by extracting with a solvent.

10 Claims, 6 Drawing Sheets

RETENTION TIME (min)

MICROORGANISM AND PRODUCTION OF CAROTINOID COMPOUNDS THEREBY

This application is a 35 U.S.C. 371 of PCT/JP02/10619, filed Oct. 11, 2002.

TECHNICAL FIELD

The invention relates to a novel microorganism strain belonging to *Thraustochytrium* species of genus *Labyrinthula*, and a method for producing astaxanthin and canthaxanthin as natural carotenoid compounds using the microorganisms.

BACKGROUND ART

Astaxanthin and canthaxanthin are dye compounds widely distributed in microbial cells, macroalgae, and miroalgae, and in various animals and plants. The compounds are used as aging retarders, detoxificants, cancer preventive agents and color improving agents of bred fish.

While astaxanthin among the natural carotenoids has been extracted from shells of crustaceans, the content of the compound in the body of these animals is quite low and extraction of the compound is very difficult. Moreover, the crustaceans are bio-resources inhabiting in limited areas of the oceans with difficulties for ensuring stable supply thereof, these resources are not suitable for industrial production.

While astaxanthin is produced by a red yeast *Phaffia rhodozyma*, growth rate of this yeast is slow and productivity of astaxanthin is small. Moreover, since the yeast has a tough cell wall, extraction of produced astaxanthin is difficult. In addition, since the content of a (3R, 3R') isomer having a chemical structure with an orientation reverse to that of natural astaxanthin is high, productivity of astaxanthin becomes inevitably low.

*Haematococcus pluvialis* are also known to produce astaxanthin. However, since the growth rate of this alga is low with a tough cell wall, productivity of astaxanthin is also low. In addition, since growth of the alga is variously restricted such that the alga is readily contaminated with bacteria, and is required to be cultured under irradiation of intense light using a special culturing apparatus, industrial production of astaxanthin involves many problems.

Canthaxanthin is distributed in a certain kind of mushroom, fish and crustacean, and are known to be produced by microorganisms belonging to genus *Brevibacterium* and genus *Rhodococcus*. While methods for obtaining canthaxanthin by chemical synthesis has been developed, the methods are not industrially used due to their low productivity.

DISCLOSURE OF THE INVENTION

The object of the present invention based on the situations above is to provide a method capable of simple and efficient large-scale production of astaxanthin and canthaxanthin from a readily available material while drawbacks of conventional methods are solved.

The inventor of the invention has made various studies on the ecology of marine microorganisms collected in the Inland Sea of Japan, and discovered novel microorganisms having high productivity of astaxanthin and canthaxanthin in their cells. The invention has been completed on the basis of the finding that astaxanthin and canthaxanthin can be efficiently produced by culturing these microorganisms.

Thus, the invention provides an isolated novel microorganism *Thraustochytrium* species CHN-3 (FERM P-18556) belonging to *Thraustochytrium Labyrinthula* which produces astaxanthin and canthaxanthin and a method for producing astaxanthin and canthaxanthin comprising the steps of: culturing the microorganism; allowing the microorganism to accumulate astaxanthin and canthaxanthin in their cells; separating the cells from the culture medium; and recovering astaxanthin and canthaxanthin from the separated cells by solvent extraction.

BEST MODE FOR CARRYING OUT THE INVENTION

The invention will be described in detail with reference to the accompanying drawings.

Figure 1:
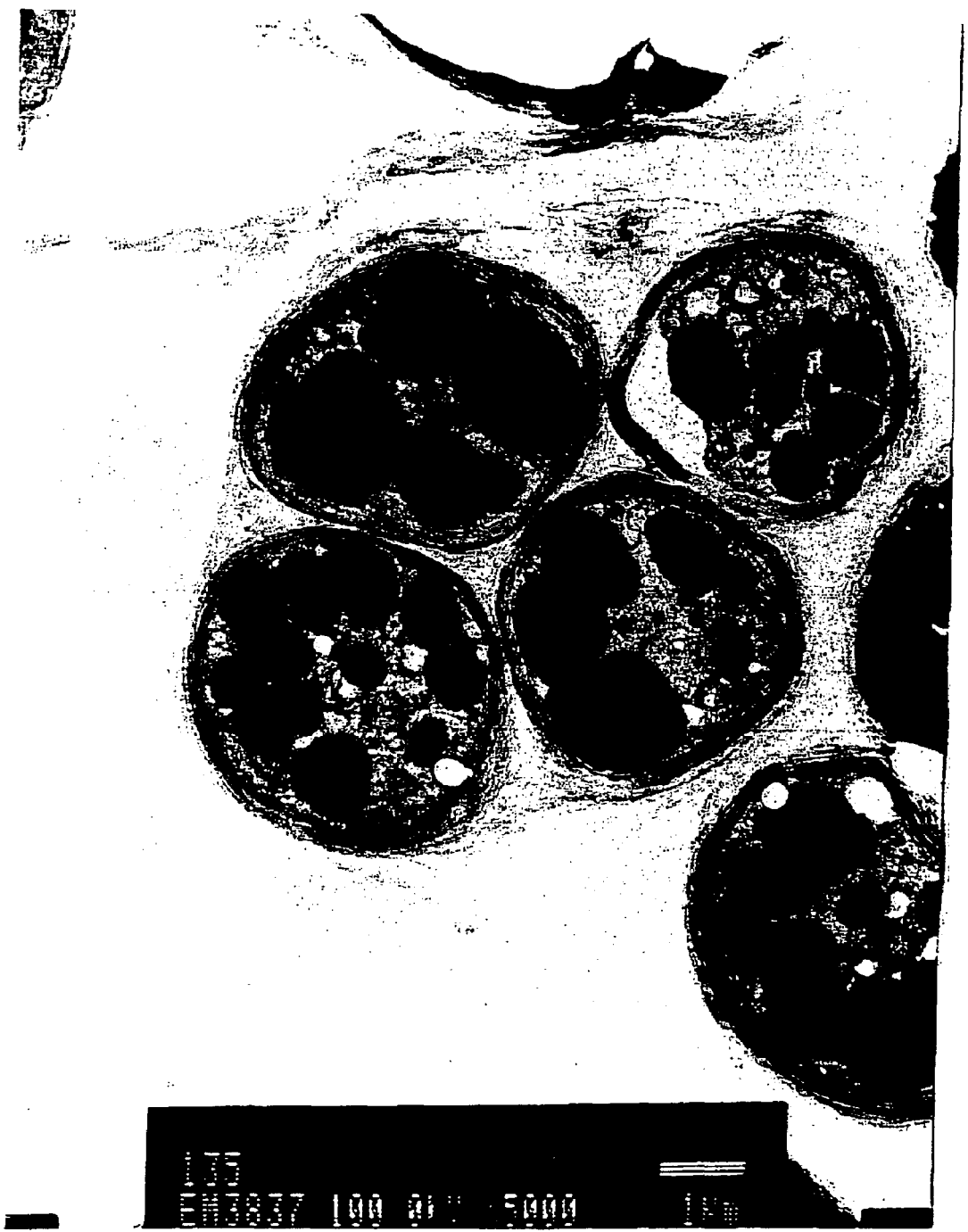
FIG. 1 is an electron microscopic photograph of the microorganism of the invention.

FIG. 1 is an electron microscopic photograph showing the shape of the microorganism of the invention. As shown in the photograph, the microorganism of the invention consists of cells having a spherical or ellipsoidal extracellular net characteristic to *Thraustochytrids Thraustochytrium*. The cell has sagenogenetosome only at one site of the cell, and intrudes into or adheres on a substrate by extending the extracellular net therefrom. The microorganism was concluded to belong to *Thraustochytrids* with reference to this characteristic.

Figure 2:
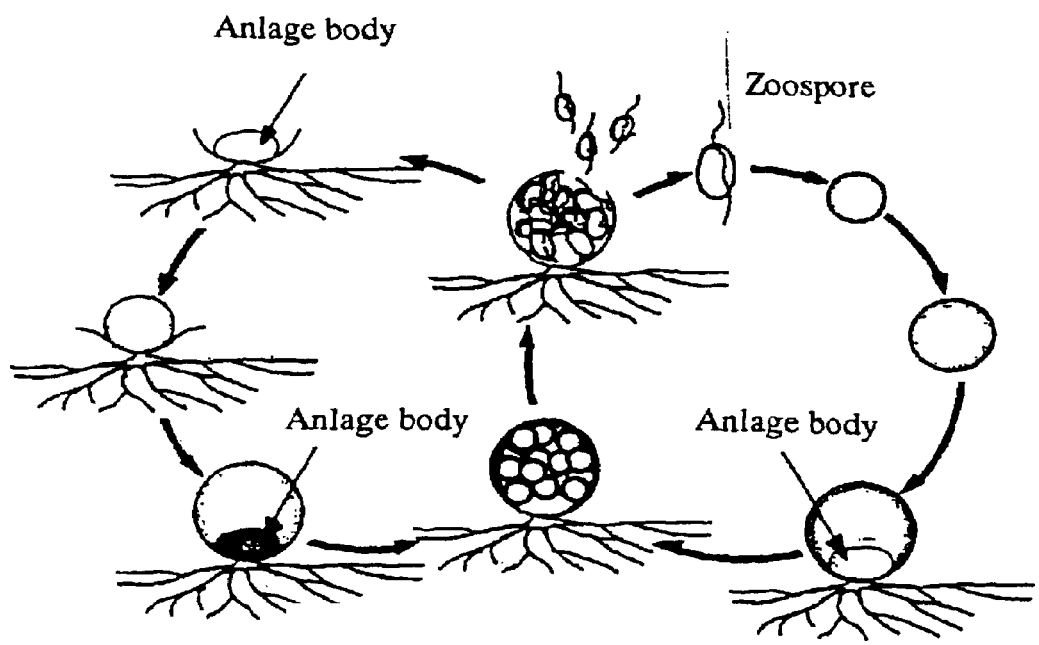
FIG. 2 shows the life cycle of *Thraustochytrium* species.

The life cycle as shown in FIG. 2 is established, and amoebae-like cells appear in a culture medium abundant in sugars such as glucose and fructose, and abundant in organic substances including proteins such as yeast extract and corn steep liquor. The microorganism is identified to be *Thraustochytrium* species since the characteristic described above is largely different from that of genus *Ulkenia*, and is different from *Schizochytrium* species in forming zoospore having two kinds of flagella. It was also confirmed that the microorganism is identified to be *Thraustochytrium* species in a phylogenetic tree based on 18SrDNA.

The microorganism of the invention is classified into *Thraustochytrium* species of genus *Labyrinthula* since the microorganism can be readily distinguished from spindle-shaped *Labyrinthula* species in that the trophocyte of the microorganism of the invention is egg-shaped or spherical. Microorganisms of this type are widely distributed in the marine environment, and are known as so-called marine microorganisms that exhibit heterotrophic proliferation.

The microorganism of the invention is readily distinguished from known microorganisms from the following microbiological properties.

I. Morphological property
(1) The cell is egg-shaped with a dimension of 10 μm.
(2) The 10 μm egg-shaped zoospore has heterokont flagellae for movement.

II. Properties on culturing
(1) The cell is pink in color with a smooth surface, and rapidly grows on a saccharic agar culture medium.
(2) The liquid culture medium becomes turbid in 24 hours, and the color of the medium turns pink.
At least 30 g of biomass are obtained per 1 liter of the culture medium.

III. Physiological properties
(1) The cell is pink in color by containing astaxanthin and canthaxanthin.
(2) The cell proliferates by utilizing organic and inorganic nitrogen sources.
(3) The optimum growth conditions include a pH of 5 to 9 and a temperature of 15 to 35° C.
(4) The cell produces large amounts of DHA and EPA using glucose and fructose.

No strains of *Thraustochytrium* species of genus *Labyrinthula* that contain DHA in a high concentration and dyes are known heretofore.

The results of bacteriological tests were all negative, and it was confirmed that the microorganisms of the invention are not classified into bacteria.

The microorganism of the invention, or *Thraustochytrium* sp. CHN-3, has been deposited at International Patent Organism Depositary, National Institute of Advanced Industrial Science and Technology (Central 6, 1-1-1 Higashi, Tsukuba-shi, Ibaraki, 305-8566, Japan) as of Oct. 9, 2001, with an accession No. FERM P-18556.

The microorganism of the invention is a single cell microorganism inhabiting in the sea with a size of about 10 μm, and is readily collected from seawater from, for example, the Inland Sea of Japan. For collecting the cells, pollens of black pine tree (*Pinus thunbergii*) are suspended in seawater and kept standing for several days followed by separation of the pollens from seawater and collecting the microbial bodies deposited on the pollens.

The cells collected as described above are subjected to pure culture in a saccharic culture medium or, namely, a culture solution abundant in sugars and peptone (for example, a medium containing 30 to 50 g of glucose and 1 g of peptone in 1 liter of seawater). The pure culture is preferably performed by aeration with a stirring while a light, preferably a blue light (wavelength 420 to 470 nm), is continuously irradiated. A red light (wavelength 600 to 700 nm) can be used concurrently with the blue light as the irradiation light.

Figure 3:
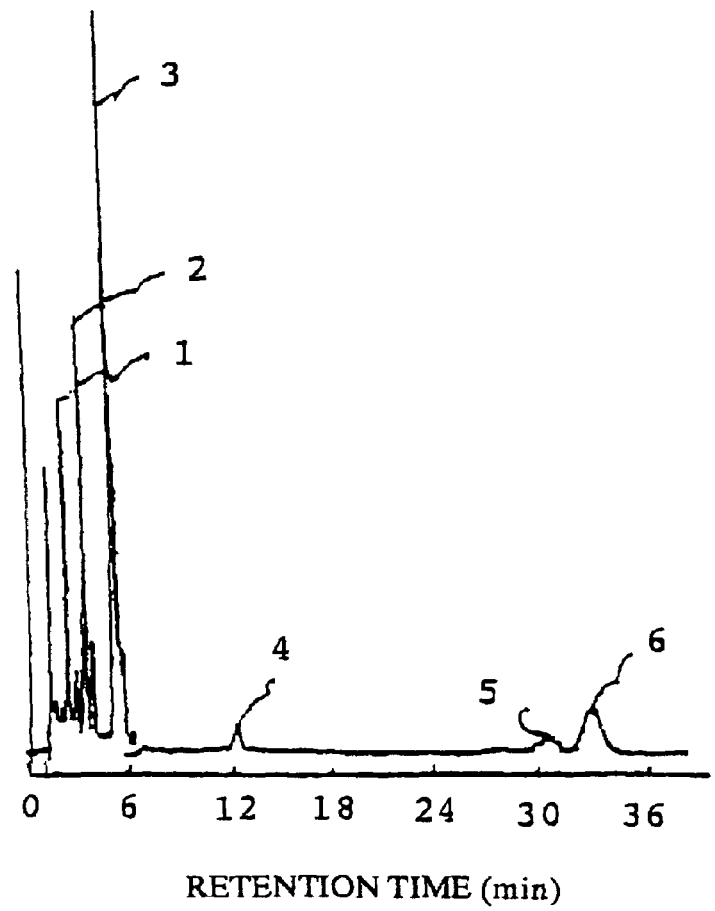
FIG. 3 is a high-performance liquid chromatogram of the culture product obtained in Example 1.

In this way, the cells of *Thraustochytrium* obtained by culturing are ground on a mortar, and the cells as ground are extracted with 100% acetone. The extract was separated by high-performance liquid chromatography equipped with an ODSC18 column, and was identified with a high-performance liquid chromatography—mass spectrometer. The chromatogram of liquid chromatography thus obtained is shown in FIG. 3 (see Example 1). It was shown from analysis that the dye consists of α- and β-carotenes, echinenone, canthaxanthin, phenocoxanthin and astaxanthin.

*Thraustochytrium* sp. CHN-3 of the invention produces α- and β-carotenes, echinenone, canthaxanthin, phenocoxanthin and astaxanthin, and colors in red by particularly accumulating a large amount of astaxanthin and canthaxanthin in the cells. No microorganisms having such ability are known among those of genus *Labyrinthula* to which *Thraustochytrium* species belongs.

*Thraustochytrium* sp. CHN-3, a microorganism classified into *Thraustochytrium* species of genus *Labyrinthula*, can be cultured in a culture medium (culture solution) containing sugars, organic nitrogen and inorganic salts.

Examples of the sugars include glucose, sucrose, fructose and those containing them, such as thick malt syrup. Examples of source of the organic nitrogen include peptone and yeast extract, while examples of the inorganic salt include sodium chloride, potassium chloride and inorganic phosphate salts.

While *Thraustochytrium* sp. CHN-3 as a microorganism is grown utilizing glucose, organic nitrogen, light energy and inorganic phosphorus, the illuminance of the light irradiation, temperature, nutrient composition in the culture medium and the amount of oxygen feed should be appropriately controlled in order to allow productivity thereof to be maximized.

The best results are obtained by culturing in a strongly alkaline medium containing high concentration of salts.

Pure culture conditions include, for example, aeration with stirring, irradiation of the blue light at an illuminance of 1,000 lux or higher, and a temperature of 20 to 30° C. or, preferably, about 28° C. The supply source of phosphorus in the medium is preferably $KH_2PO_4$, and the concentration thereof is in the range of 0.1 to 3 g/liter. The cells are cultured in a medium having a composition in the range for permitting microorganisms of genus *Labyrinthula* to grow (60 g of glucose, 1 g of peptone and 1 g of $KH_2PO_4$ in 1 liter of seawater, or 30 g of glucose, 1 g of peptone and 1 g of yeast extract in 1 liter of seawater). Productivity of each of astaxanthin and canthaxanthin can be selectively enhanced by adjusting the concentration of the nutrient components in the culture medium in a specified range at the end of the growth of the cells.

The inorganic salts used in the method of the invention include sodium chloride and potassium chloride, and the concentration of the salts is preferably 4 to 10% by weight.

Examples of alkaline substances used in the method of the invention include potassium carbonate and sodium carbonate. The pH of the culture medium is desirably 9 or higher or, preferably, about 10. While the pH of the culture medium available is in the range of 4 to 12 or, preferably, 6 to 10, productivity increases, as the pH is higher. The yield of astaxanthin is remarkably increased by adding vitamin compounds, particularly thiamine, in a concentration of up to 5 mg/liter in the culture medium in addition to the additives described above. Fatty acid esters of astaxanthin may be produced when the amount of addition of thiamine is large, although the amount of production of the fatty acid esters is small.

As described above, productivity of astaxanthin and canthaxanthin can be further increased by strongly stimulating proliferation of *Thraustochytrium* species by changing the culture conditions, particularly by changing the nitrogen source composition. Examples of the nitrogen source used in the invention include urea, ammonia and potassium nitrate, and the amount of addition of them is up to 2% by weight or, preferably, 1% by weight.

Accordingly, it is advantageous to permit production ability of astaxanthin and canthaxanthin of the microorganism to be exhibited in maximum by maintaining the growth environment of *Thraustochytrium* species in an ultimate condition of high salt concentration, in order to produce astaxanthin and canthaxanthin in high yields. It is effective for this object to adjust the initial concentration of yeast extract low.

The content of astaxanthin is increased to as high as 1.537 mg in 1 g of dry cells by reducing the amount of yeast extract as a nitrogen source in the culture medium. The culture medium is changed to a yeast extract-free culture solution when the content of astaxanthin is increased. Then, the content of astaxanthin is increased to about 2 mg per 1 g of the dry cells, since no nitrogen introduced into the cells of *Thraustochytrium* species is contained in the culture medium.

When astaxanthin is produced by the method of the invention, the cells are cultured in a culture medium supplemented with yeast extract at the initial stage, and are cultured in a nitrogen source-free medium without replenishing the nitrogen source after yeast extract has been consumed. Culturing in the nitrogen source-free medium as described above permits the yield of astaxanthin to be increased by five times or more as much as the yield obtained by adding the nitrogen source in the culture medium. The yield of astaxanthin may be further increased by culturing the cells in an aerobic condition abundant in oxygen.

Figure 6:
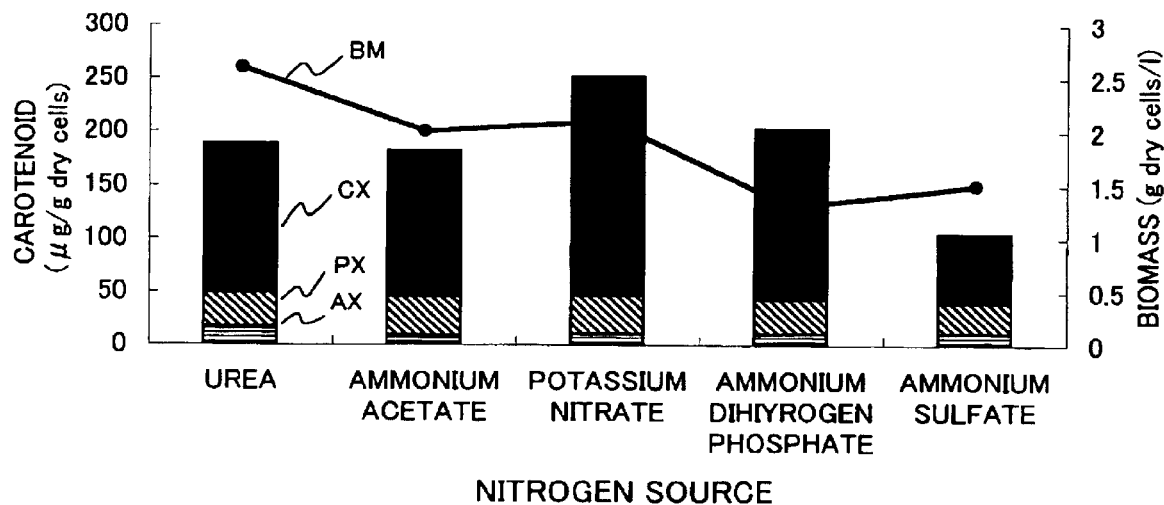
FIG. 6 is a graph showing the relation between the amount of production of carotenoid and the kind of the nitrogen source. In the graph, CX denotes canthaxanthin and PX denotes phenocoxanthin. The definitions are the same in the graphs to follow.

For producing canthaxanthin, the microorganism is cultured in a medium supplemented with yeast extract at the initial stage, and the nitrogen source is replenished after yeast extract has been consumed in order to maintain the culture condition in which the nitrogen source is always contained and which is slightly acidic. The productivity of canthaxanthin increases by culturing in which inorganic nitrogen such as potassium nitrate is added as the nitrogen source (see FIG. 6). The yield of canthaxanthin is increased by 4 to 5 times or more as much as the yield when the cells are cultured in a nitrogen-free medium.

For efficiently extracting astaxanthin and canthaxanthin thus obtained from the cells of the microorganism containing a large amount of astaxanthin and canthaxanthin, the cells are preferably extracted with a solvent such as acetone, chloroform, methyl alcohol and hexane, or with a mixed solvent thereof.

Thus, astaxanthin and canthaxanthin produced are separated from the cells into the extract. Then, the extract is applied on a column filled with silica gel to adsorb carotenoid, which is eluted with a mixed solvent of methyl alcohol or hexane/chloroform mixed solvent to recover astaxanthin and canthaxanthin in 100% yield. The mixed solvent of methyl alcohol used contains 90 to 95% by volume of methyl alcohol with a balance of chloroform. A mixed solvent comprising 60 to 65% by volume of chloroform with a balance of hexane is used when a hexane-chloroform mixed solvent is used for elution.

While the invention is described in detail hereinafter with reference to examples, the invention is by no means limited to these examples.

EXAMPLE 1

Pure *Thraustochytrium* species CHN-3 purified from *Thraustochytrium* species CHN-1 collected by suspending the pollens of *Pinus thunbergii* in seawater sampled from the coast of Nagahama district of the seacoast of the Inland Sea of Japan was inoculated to a saccharic culture medium (pH 5.0) containing 60 g/liter of glucose, 1 g/liter of peptone, 1 g/liter of potassium dihydrogen phosphate and 1 g/liter of phosphorus as phosphate ions in seawater. The cells were cultured at a temperature of 28° C. for 6 days under aeration with stirring while a white light (the light from a fluorescent lamp) is irradiated at an intensity of 1000 lux. The culture solution obtained was centrifuged to collect the cells of the microorganism. The electron microscopic photograph of the cells obtained as described above is shown in FIG. 1.

The cells were extracted with acetone, chloroform and methyl alcohol, and the extract was passed through a column filled with silica gel (trade name Wako gel, manufactured by Wako Pure Chemical Industries, Ltd.) to adsorb the products. Then, the column was eluted successively with hexane-chloroform and methyl alcohol, and 8.8 mg of astaxanthin and 6.5 mg of canthaxanthin per one liter of the culture medium were obtained. The contents of astaxanthin and canthaxanthin per 1 g of dry cells were 2.8 mg and 2.0 mg, respectively. FIG. 3 shows a chromatogram of high-performance liquid chromatography of carotenoid obtained in Example 1. The reference numerals in the drawing correspond to the following compounds.

1: astaxanthin, 2: phenocoxanthin, 3: canthaxanthin,
4: echinenone, 5: α-carotene, 6: β-carotene.

EXAMPLE 2

*Thraustochytrium* species CHN-3 was cultured at a temperature of 23° C. for 6 days using a culture medium containing 50 g/liter of glucose, 1 g/liter of peptone and 1 g/liter of potassium dihydrogen phosphate in seawater under the following conditions; (a) rotation-vibration culturing at 100 rpm under a white light illumination at an illuminance of 1000 lux, (b) rotation-vibration culturing at 100 rpm in dark, (c) static culturing at an illuminance of 1000 lux, and (d) aeration culturing with stirring at an illuminance of 1000 lux. The results are shown in Table 1.

TABLE 1

|  |  | Culture condition | | | |
| --- | --- | --- | --- | --- | --- |
|  |  | (a) | (b) | (c) | (d) |
| Products | Astaxanthin (mg/g dry cells) | 0.8-1.0 | 0.2-0.5 | 0.1> | 1.0-1.8 |
|  | Biomass (g dry cells/litter) | 2.01-2.62 | 1.37-1.46 | 0.26-0.39 | 2.46-3.10 |

Table 1 shows that substantially no astaxanthin is produced by static culturing. Light irradiation affords more astaxanthin in rotation-vibration culture. The yield of astaxanthin could be increased as much as 1.8 times by increasing the oxygen concentration by aeration. Employing an aerobic condition, or enhancing the oxygen concentration in the culture medium, permits the production ratio of astaxanthin to be enhanced.

EXAMPLE 3

Figure 4:
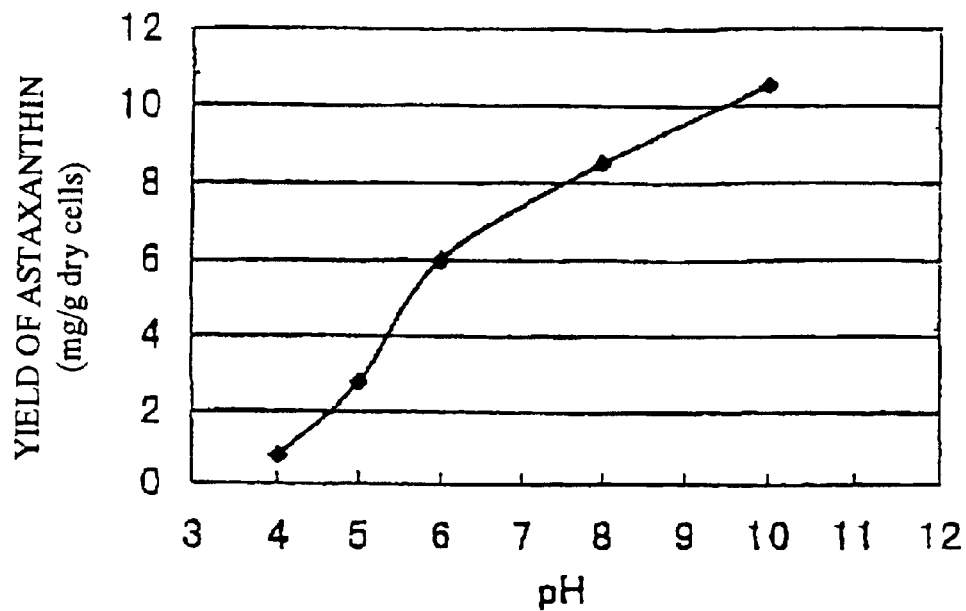
FIG. 4 is a graph showing the relation between the amount of produced astaxanthin and pH of the culture medium.

Culturing was continued for 14 days by the same test culturing as in Example 1, except that the pH of the sugar-rich culture medium used in Example 1 was changed using aqueous hydrochloric acid solution and aqueous sodium hydroxide solution, and productivity of astaxanthin at each pH was determined. The results are shown in the graph in FIG. 4. The graph shows that the productivity of astaxanthin increased, as the pH was increased.

EXAMPLE 4

Various culture solutions each different from the orders in the sodium chloride concentration were prepared by adding sodium chloride in a sugar-rich culture medium (referred to as a sugar medium hereinafter) containing 30 g/liter of glucose, 1 g/liter of peptone and 1 g/liter of yeast extract in seawater (sodium chloride concentration 3.2%). *Thraustochytrium* species CHN-3 used in Example 1 was inoculated to the culture solutions, and was cultured for 6 days by aeration with stirring at a temperature of 28° C. under white light illumination at an illuminance of 1000 lux. Then, each of the culture solutions was centrifuged to collect the microorganism cells. The yields of the biomass and carotenoid thus obtained were 2 to 5 g/liter and 0.5 to 1 mg/g, respectively.

The cells obtained were extracted with acetone, chloroform and methyl alcohol, and the extract was analyzed by high-performance liquid chromatograph equipped with an ODS C18 column. The contents of astaxanthin and canthaxanthin in the cells (the concentrations in dry cells) were 1.0 to 2.0 mg and 0.3 to 0.5 mg, respectively, per 1 g of dry cells.

EXAMPLE 5

Figure 7:
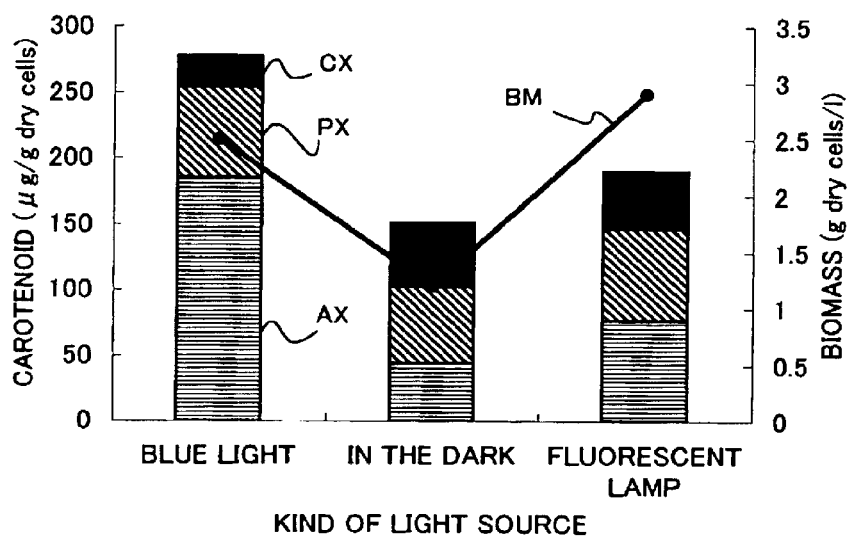
FIG. 7 is a graph showing the relation between the amount of production of carotenoid and presence/absence of light and types of the light sources.

*Thraustochytrium* species CHN-3 was cultured using a culture medium containing 50 g of glucose, 1 g of peptone and 1 g of potassium dihydrogen phosphate in 1 liter of seawater, and by stirring the medium by feeding air with shaking at a rotation speed of 100 rpm at a temperature of 23° C. under irradiation of a white light from a fluorescent lamp or blue light (wavelength 470 nm) at an illuminance of 1000 lux, or in dark. The results are shown in the graph in FIG. 7.

The graph shows that a small amount of astaxanthin is produced in dark. More astaxanthin could be obtained by irradiating the blue light than irradiating a white light in the rotation-vibration culturing under light irradiation. This shows that increasing the intensity of irradiation of the blue light to the medium enhances the production ratio of astaxanthin.

EXAMPLE 6

Figure 5:
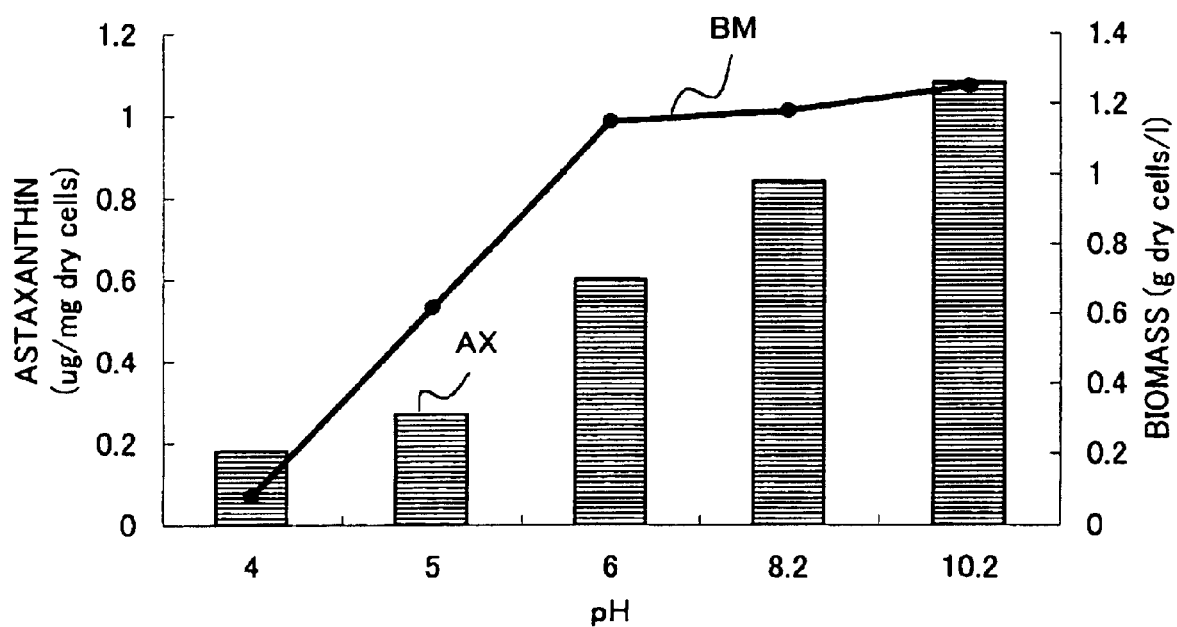
FIG. 5 is a graph showing the relation between the amounts of production of astaxanthin in Example 6 and biomass, and pH of the culture medium. In the graph, AX denotes astaxanthin and BM denotes the biomass. The definitions are the same in the graphs to follow.

Culturing was continued for 14 days under the same conditions as in Example 4, except that the pH of the sugar medium was changed. The results are shown in the graph in FIG. 5. The graph shows that productivity of astaxanthin generally increases in the pH range of 4 to 10, as the pH increases.

EXAMPLE 7

Figure 8:
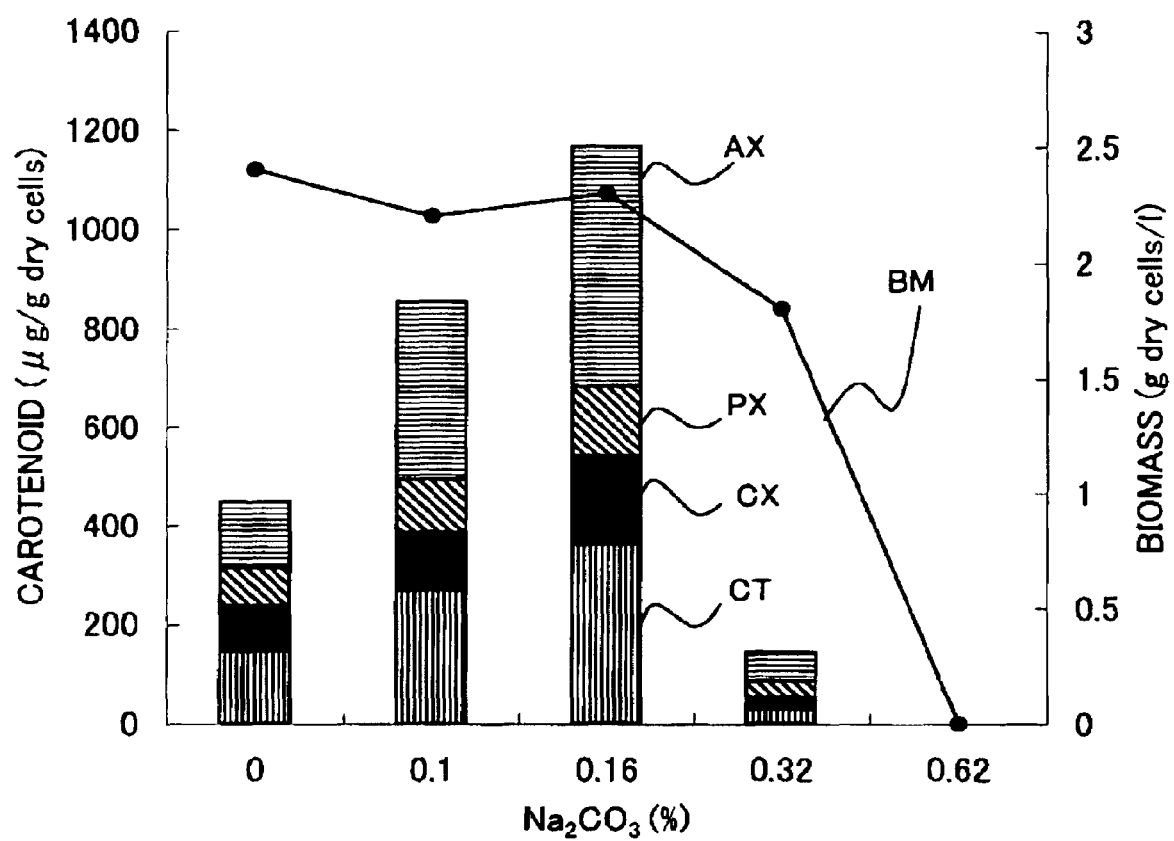
FIG. 8 is a graph showing the relation between the amount of production of carotenoid and alkali concentration. In the graph, CT denotes carotene.

Culturing was continued for 7 days under the same conditions as in Example 4 except that the amount of addition of $Na_2CO_3$ in the sugar medium was changed and the amount of the biomass, and productivity of astaxanthin and canthaxanthin were determined. The results are shown in the graph in FIG. 8. The graph shows that the amount of the biomass and productivity of astaxanthin are increased, as the concentration of $Na_2CO_3$ increases up to 1.6%.

EXAMPLE 8

Figure 9:
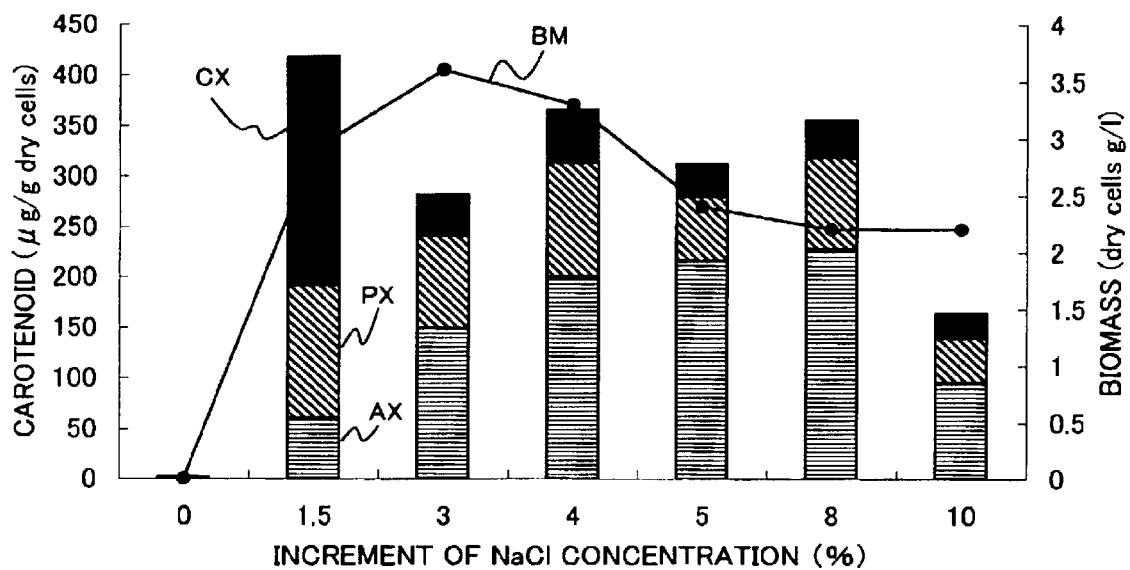
FIG. 9 is a graph showing the relation between the amount of production of carotenoid and salt concentration.

A culturing test was continued for 7 days under the same conditions as in Example 4 except that the amount of addition of NaCl in the sugar medium was changed and the amount of the biomass, and productivity of astaxanthin and canthaxanthin were determined. The productivity at each increment of the NaCl concentration is shown in the graph in FIG. 9. The graph shows that the amount of the biomass and productivity of astaxanthin are increased as the concentration of NaCl increases up to 6%.

EXAMPLE 9

Figure 10:
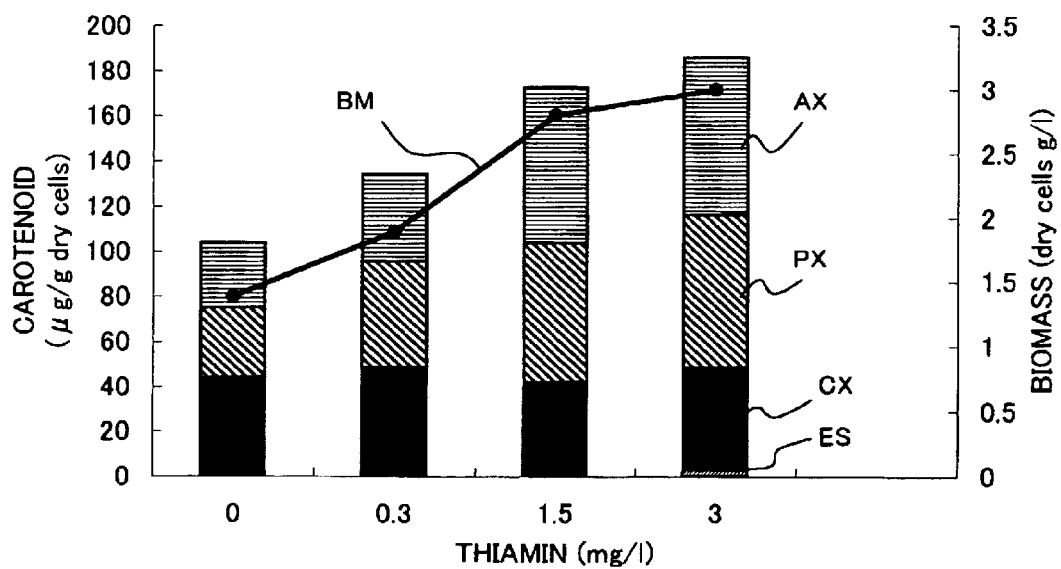
FIG. 10 is a graph showing the relation between the amount of production of carotenoid and the amount of addition of thiamine. In the graph, ES denotes astaxanthin fatty acid ester.

A culturing test was continued for 7 days under the same conditions as in Example 4, and the amount of the biomass, and productivity of astaxanthin and canthaxanthin were determined, except that thiamine as a vitamin compound was added in the sugar medium by changing the amount of addition thereof. The results are shown in the graph in FIG. 10. The graph shows that the amount of the biomass and productivity of astaxanthin are increased, as the amount of addition of thiamin is increased. It is also shown that fatty acid esters of astaxanthin (denoted by ES) as by-products are increased, as the thiamin concentration increases.

INDUSTRIAL APPLICABILITY

The invention provides a method for culturing pure *Thraustochytrium* species microorganisms particularly containing high concentrations of astaxanthin and canthaxanthin in a large scale, and a method for simply extracting and separating astaxanthin and canthaxanthin. The invention enables to provide astaxanthin, canthaxanthin or a mixture containing a desired proportion of astaxanthin and canthaxanthin in a high yield and high concentration.

The invention claimed is:

1. A biologically pure microorganism strain *Labyrinthula Thraustochytrium* FERM P-18556.

2. A method for producing astaxanthin and canthaxanthin comprising the steps of:
   culturing the microorganism strain according to claim 1 in a culture medium to accumulate astaxanthin and canthaxanthin in the microorganism cells,
   isolating the microorganism cells from the culture medium, and
   recovering astaxanthin and canthaxanthin from the isolated microorganism cells by solvent extraction.

3. The method according to claim 2, wherein pH of the culture medium is maintained at 4 to 12, and the microorganism strain is cultured under an aerobic condition.

4. The method according to claim 2, wherein the culture medium contains a sugar selected from the group consisting of sucrose, glucose and fructose.

5. The method according to claim 2, wherein the microorganism strain is cultured under irradiation of a light.

6. The method according to claim 5, wherein the light used for light irradiation is a blue light having a wavelength of 420 to 470 nm.

7. The method according to claim 5, wherein the light used for light irradiation is a mixed light of a blue light having a wavelength of 420 to 470 nm and a red light having a wavelength of 600 to 700 nm.

8. The method according to claim 2, wherein the culture medium contains a vitamin compound.

9. The method according to claim 8, wherein the vitamin compound is thiamine.

10. The method according to claim 2, wherein the culture medium contains a nitrogen compound selected from the group consisting of urea, ammonia and potassium nitrate.

* * * * *